(12) United States Patent
Finnestad

(10) Patent No.: US 8,397,933 B2
(45) Date of Patent: Mar. 19, 2013

(54) MEDICAL WASTE RECEPTABLE

(75) Inventor: Mark Brian Finnestad, Franklin, MA (US)

(73) Assignee: Covidien LP, Mansfield, MA (US)

( * ) Notice: Subject to any disclaimer, the term of this patent is extended or adjusted under 35 U.S.C. 154(b) by 233 days.

(21) Appl. No.: 12/853,372

(22) Filed: Aug. 10, 2010

(65) Prior Publication Data
US 2012/0037628 A1 Feb. 16, 2012

(51) Int. Cl.
*B65D 51/18* (2006.01)

(52) U.S. Cl. .................. 220/254.3; 220/212; 220/254.9; 220/324; 220/326; 220/521; 220/908; 206/1.5; 206/362; 206/366; 206/370; 232/30; 232/31; 232/32; 232/45; 232/47; 232/57; 232/58; 232/60; 232/62

(58) Field of Classification Search .................. 220/212, 220/254.3, 324, 326, 908, 254.9, 521; 206/1.5, 206/366, 370, 362; 232/30, 31, 32, 45, 47, 232/57, 58, 60, 62
See application file for complete search history.

(56) References Cited

U.S. PATENT DOCUMENTS

| | | | |
|---|---|---|---|
| 4,453,648 A | 6/1984 | Harris et al. | |
| 4,580,688 A | 4/1986 | Harris et al. | |
| 4,714,168 A | 12/1987 | Johnson et al. | |
| 4,715,498 A | 12/1987 | Hanifl | |
| 4,779,728 A | 10/1988 | Hanifl et al. | |
| 4,890,733 A | 1/1990 | Anderson | |
| 5,076,429 A | 12/1991 | Patrick et al. | |
| 5,154,345 A | 10/1992 | Shillington | |
| 5,240,108 A | 8/1993 | Tonna | |
| 5,346,086 A | 9/1994 | Harris | |
| 5,419,435 A | 5/1995 | Perzan et al. | |
| 5,494,158 A * | 2/1996 | Erickson | 206/366 |
| 5,494,186 A | 2/1996 | Marsh | |
| 5,570,783 A | 11/1996 | Thorne et al. | |
| 5,647,502 A | 7/1997 | Marsh | |
| 5,848,692 A | 12/1998 | Thorne et al. | |
| 5,947,285 A | 9/1999 | Gaba et al. | |
| 6,250,465 B1 | 6/2001 | Daniels et al. | |
| 6,283,909 B1 | 9/2001 | Sharp | |
| 7,516,844 B2 | 4/2009 | Erickson et al. | |
| 7,600,638 B2 | 10/2009 | Finnestad et al. | |
| 7,694,822 B2 | 4/2010 | Sullivan et al. | |
| 2005/0269227 A1 * | 12/2005 | Erickson et al. | 206/366 |
| 2012/0037626 A1 | 2/2012 | Finnestad | |

* cited by examiner

*Primary Examiner* — Anthony Stashick
*Assistant Examiner* — Elizabeth Volz
(74) *Attorney, Agent, or Firm* — Lisa E. Winsor, Esq.

(57) ABSTRACT

A lid covering an interior of a medical waste receptacle base. The lid includes an intermediate waste repository connected to the cover. The repository is moveable between a holding position adapted for holding waste segregated from the receptacle base interior, and a dumping position adapted for biasing waste by gravity into the receptacle base interior.

19 Claims, 5 Drawing Sheets

MEDICAL WASTE RECEPTABLE

FIELD OF THE INVENTION

The present invention relates to a medical waste receptacle, and more particularly to a receptacle having an intermediate waste repository.

BACKGROUND

Healthcare providers and biomedical research facilities generate significant quantities of contaminated waste that are a potential source of disease and infection. Examples of such waste include syringes, needles, intravenous bags, catheters, wound care products, and other disposable patient care products. It is important that medical waste disposal containers limit access to their contents during use to prevent users from contacting the contaminated waste. Accordingly, there is a need for such containers.

SUMMARY

The present invention relates to a lid covering an interior of a medical waste receptacle base. The lid includes a cover sized and shaped for covering the interior of the medical waste receptacle base. The cover has an opening sized for passing medical waste through it. The lid also includes an intermediate waste repository connected to the cover. The repository is moveable between a holding position adapted for holding waste segregated from the receptacle base interior, and a dumping position adapted for biasing waste by gravity into the receptacle base interior. The lid also includes a closure sized for blocking the opening operatively connected to the cover for movement between an open position, in which the closure is at least partially out of alignment with the opening to allow medical waste to pass through the opening toward the intermediate waste repository, and a closed position, in which the closure is aligned with the opening to block the opening to prevent medical waste from passing through the opening. The lid also includes a link operatively connecting the closure and the intermediate waste repository so the intermediate waste repository moves to the dumping position as the closure moves to the closed position and so the intermediate waste repository moves to the holding position as the closure moves to the open position.

In another aspect, the present invention relates to a medical waste receptacle including a base having an interior sized and shaped for receiving medical waste. The medical waste receptacle also induces a cover sized and shaped for covering the interior of the base. The cover has an opening sized for passing medical waste through it. The medical waste receptacle also includes an intermediate waste repository connected to the cover. The repository is moveable between a holding position adapted for holding waste segregated from the receptacle base interior, and a dumping position adapted for biasing waste by gravity into the receptacle base interior. The medical waste receptacle also includes a closure sized for blocking the opening operatively connected to the cover for movement between an open position, in which the closure is at least partially out of alignment with the opening to allow medical waste to pass through the opening toward the intermediate waste repository, and a closed position, in which the closure is aligned with the opening to block the opening to prevent medical waste from passing through the opening. The medical waste receptacle also includes a link operatively connecting the closure and the intermediate waste repository. The link moves the intermediate waste repository to the dumping position as the closure moves to the closed position and moves the intermediate waste repository to the holding position as the closure moves to the open position.

In yet another aspect, the present invention includes a lid covering an interior of a medical waste receptacle base. The lid includes a cover sized and shaped for covering the interior of the medical waste receptacle base. The cover has an opening sized for passing medical waste through it. The lid also includes a closure sized for blocking the opening operatively connected to the cover for movement between an open position, in which the closure is at least partially out of alignment with the opening to allow medical waste to pass through the opening, and a closed position, in which the closure is aligned with the opening to block the opening to prevent medical waste from passing through the opening. The lid also includes an intermediate waste repository operatively connected to the closure so the repository moves from a holding position adapted for holding waste segregated from the receptacle base interior to a dumping position adapted for biasing waste by gravity into the receptacle base interior as the closure moves to the open position and so the repository moves from the dumping position to the holding position as the closure moves to the closed position. The closure moves at least partway from the open position to the closed position before the repository moves from the holding position toward the dumping position.

In a further aspect, the present invention includes a medical waste receptacle including a base having an interior sized and shaped for receiving medical waste. The medical waste receptacle also includes a cover sized and shaped for covering the interior of the base. The cover has an opening sized for passing medical waste through it. The medical waste receptacle also includes a closure sized for blocking the opening operatively connected to the cover for movement between an open position, in which the closure is at least partially out of alignment with the opening to allow medical waste to pass through the opening, and a closed position, in which the closure is aligned with the opening to block the opening to prevent medical waste from passing through the opening. The medical waste receptacle also includes an intermediate waste repository operatively connected to the closure so the repository moves from a holding position adapted for holding waste segregated from the interior to a dumping position adapted for biasing waste by gravity into the interior as the closure moves to the open position and so the repository moves from the dumping position to the holding position as the closure moves to the closed position. The closure moves at least partway from the open position to the closed position before the repository moves from the holding position toward the dumping position.

BRIEF DESCRIPTION OF THE DRAWINGS

Corresponding reference characters indicate corresponding parts throughout the drawings.

DETAILED DESCRIPTION OF THE DRAWINGS

Figure 1:
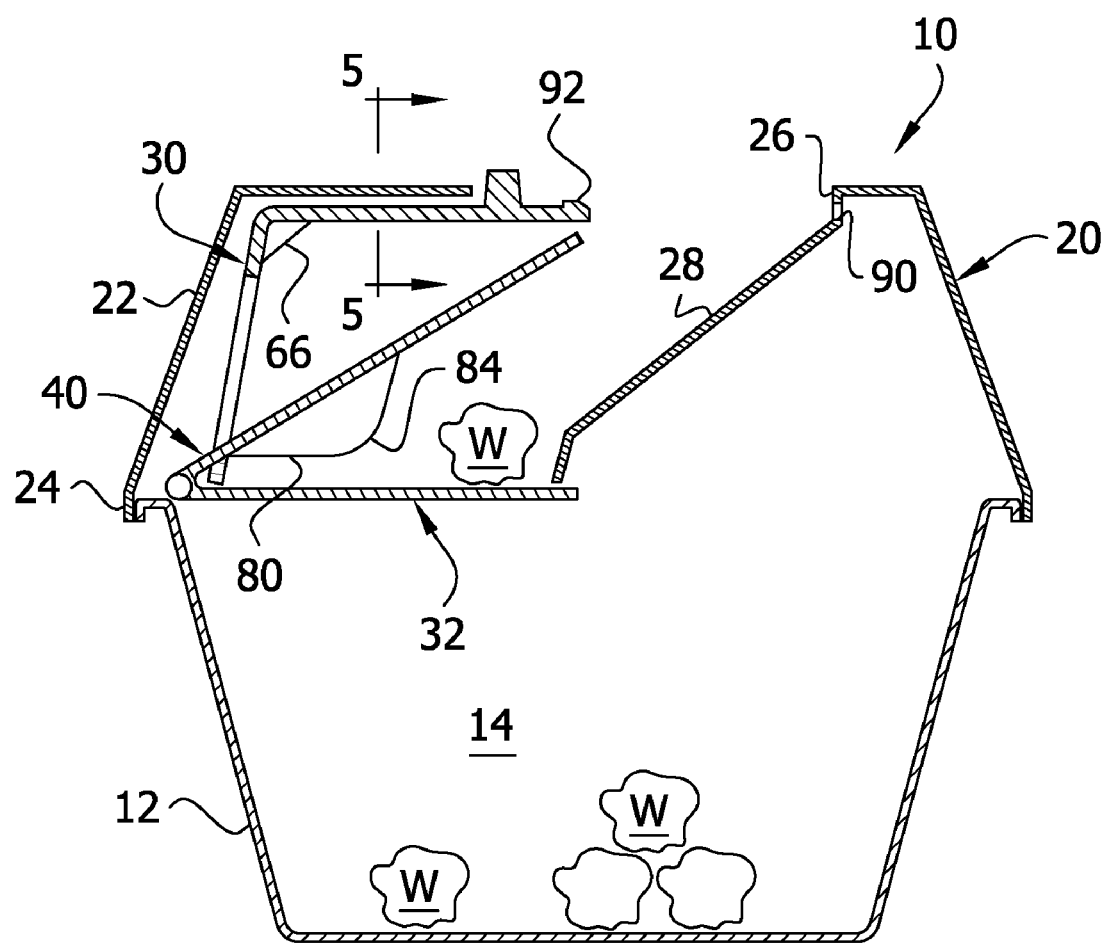
FIG. 1 is a vertical cross section of a medical waste receptacle of the present invention shown with a closure thereof in an open position.

Referring to FIG. 1, a medical waste receptacle is generally designated by the reference number 10. The receptacle 10 includes a conventional base 12 having an interior 14 sized and shaped for receiving medical waste W. Medical waste W is stored in the interior 14 of the base 12 until the receptacle 10 is deemed ready for disposal using conventional procedures. Because the base 12 is conventional, it will not be described in further detail.

The receptacle 10 also includes a lid, generally designated by 20, for covering the interior 14 of the base 12. The lid 20 includes a cover 22 sized and shaped for covering the interior of the medical waste receptacle base 12. The lid 20 has a rim 24 extending around the cover 22 for attaching the lid 20 to the base 12. The cover 22 has an opening 26 sized for passing medical waste W so a user can insert the waste into the interior 14 of the base without removing the lid 20 from the base 12. A chute 28 extends downward from the cover 22 immediately below the opening 26 to direct the medical waste W dropped through the opening downward and laterally away from the opening to the interior 14 of the base 12. The lid 20 may be removably or permanently attached to base 12. In one embodiment, the lid 20 is integrally formed with base 12.

Figure 2:
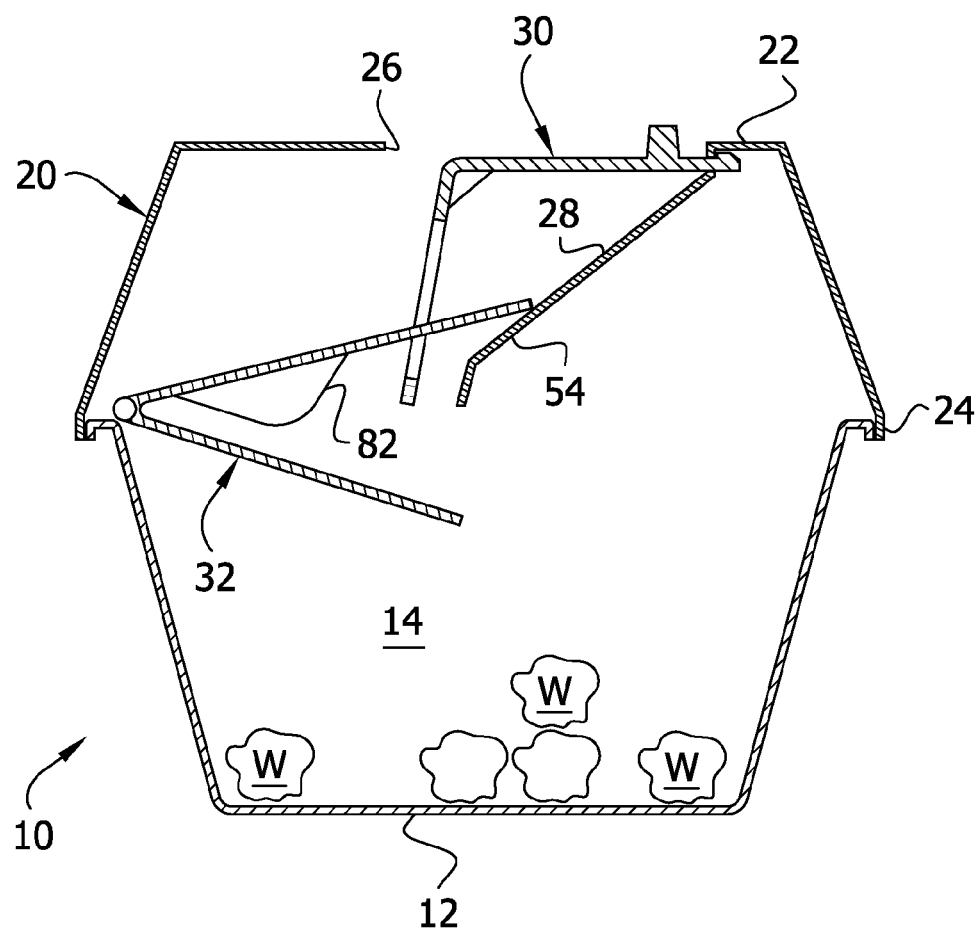
FIG. 2 is a vertical cross section of the receptacle shown with the closure in a closed open position.

The lid 20 also includes a closure, generally designated by 30, sized for selectively blocking the opening 26 in the cover 22. The closure 30 is operatively connected to the cover 22 for movement between an open position as shown in FIG. 1 and a closed position as shown in FIG. 2. In the open position (FIG. 1), the closure 30 is at least partially out of alignment with the opening 26 in the cover 22 to allow medical waste W to pass through the opening to the interior 14 of the base 12. In the closed position (FIG. 4), the closure 30 is aligned with the opening 26 in the cover 22 to block the opening and to prevent medical waste W from passing through the opening to the interior 14 of the base 12.

The lid 20 also includes an intermediate waste repository, generally designated by 32, pivotally connected to the closure 30 so the repository moves between a holding position as shown in FIG. 1 and a dumping position as shown in FIG. 2. The chute extends into the repository 32 when the repository is in the holding position (FIG. 1) so the repository collects waste W and holds it separate from the interior 14 of the base 12. In the dumping position (FIG. 2), the intermediate waste repository 32 is rotated downward so waste W is biased out of the repository and into the interior 14 of the base 12 by gravity. As will be explained more thoroughly below, the repository 32 moves from the holding position to the dumping position as the closure 30 moves to the closed position. The repository 32 moves from the dumping position to the holding position as the closure 30 moves to the open position. Because a mechanical link, generally designated by 40, operatively connects the closure 30 and the repository 32, the closure moves at least part way from the open position to the closed position before the repository moves from the holding position to the dumping position. Likewise, the closure 30 moves at least part way from the closed position to the open position before the repository 32 moves from the dumping position to the holding position. By moving as described, the repository 32 limits or blocks users from contacting medical waste W held in the interior 14 of the base 12 when the closure 30 is in the open position. When the closure 30 is in the closed position, the closure prevents users from contacting medical waste W held in the interior 14 of the base 12. Thus, users are protected from contacting medical waste W held in the interior 14 of the base 12 whenever using the medical waste receptacle 10.

Figure 3:
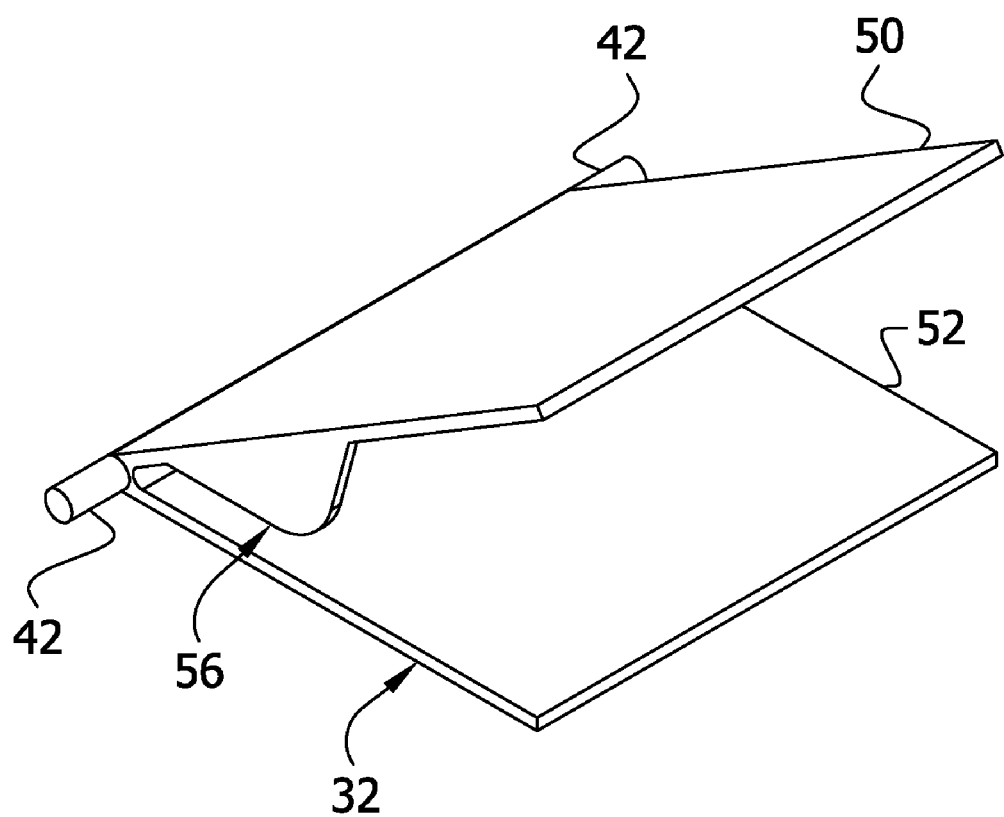
FIG. 3 is a perspective of a hopper of the receptacle.

As shown in FIG. 3, the intermediate waste repository 32 in one embodiment is a V-shaped hopper having pins 42 extending from each end for pivotally mounting the hopper on the cover 22. The pins 42 are held in corresponding openings (not shown) provided in the cover 22 to allow the hopper to pivot between the holding position shown in FIG. 1 and the dumping position shown in FIG. 2. The hopper includes an upper wall 50 and an opposing lower wall 52. The upper wall 50 engages a lower end 54 of the chute 28 when the repository 32 is in the dumping position. The lower wall 52 engages the lower end 54 of the chute 28 when the repository is in the holding position. A cam, generally designated by 56, extends downward from a lower surface of the upper wall 50 at each end of the hopper to a camming surface 58. The cam 56 forms part of the link 40 connecting the repository 32 and closure 30.

Figure 4:
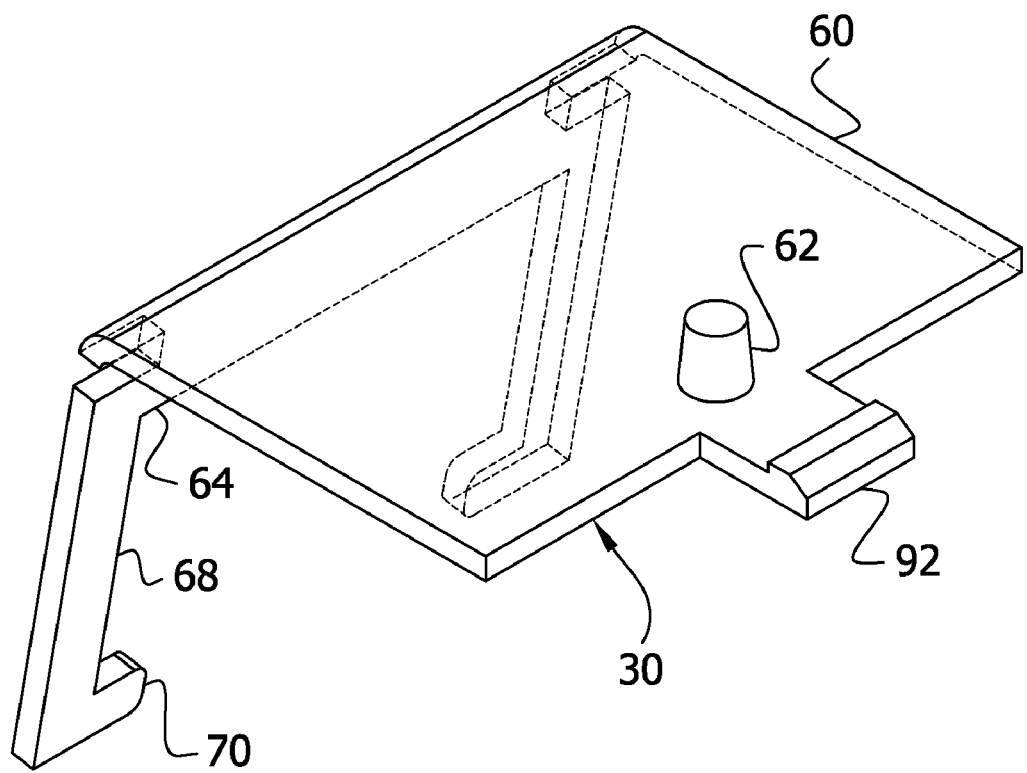
FIG. 4 is a perspective of a closure of the receptacle.

FIG. 4 shows the closure 30 includes a door 60 that selectively blocks the opening 26 in the cover 22. A knob 62 extends upward from a leading margin of the door 60 to assist the user in selectively maneuvering the door between the open and closed positions. A panel 64 extends downward from a trailing edge of the door 60, and gussets 66 (FIG. 1) extend between the panel and door to strengthen the resulting connection. Arms 68 extend downward from each end of the panel 64 adjacent the ends of the hopper. A cam follower 70 extends inward from a lower end of each arm 68 between the upper wall 50 and the lower wall 52. The followers 70 engage the camming surface 58 of the cams 56 extending downward from the upper wall 50 of the hopper. Together, the cams 56 and followers 70 form the link 40 connecting the repository 32 and closure 30. As will be explained in more detail, the cams and followers control pivoting of the hopper as the closure 30 is opened and closed.

Figure 5:
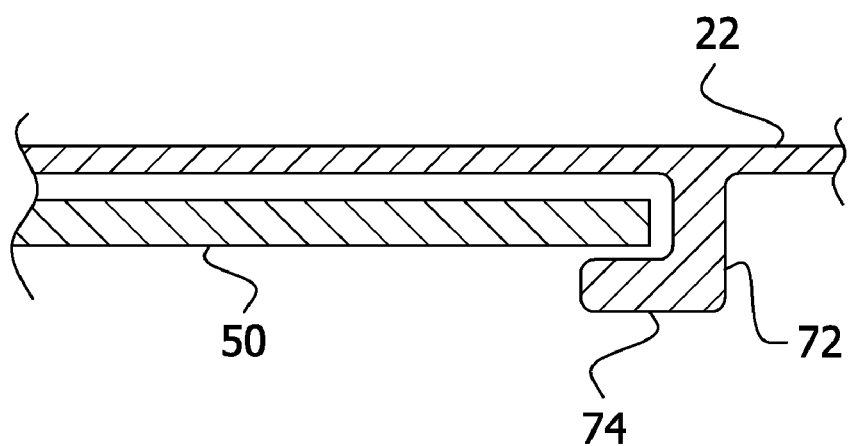
FIG. 5 is a cross section taken along line 5-5 of FIG. 1.

As shown in FIG. 5, parallel rails 72 extend downward from the cover 22 on each side of the door 60 for guiding the door between the open and closed positions. Flanges 74 extend inward from lower edges of the rails 72 to hold the door 60 in place against the cover. As a result of the rails 72 and flanges 74, the closure is slidably attached to the lid 20 for movement between the open and closed positions. Because these features are conventional, they will not be described in further detail.

As shown in FIG. 1, a first portion 80 of the camming surface 58 extends parallel to a direction indicated by the letter A in which the door 60 slides when moving from the open position to the closed position. As will be apparent to those skilled in the art, this configuration ensures the repository 32 stays in the holding position as the door 60 moves at least part way from the open position to the closed position, Preferably, the repository 32 stays in the holding position until the door 60 nears the closed position. Accordingly, a user is prevented from accessing the contents of the interior 14 of the receptacle 10 as the door 60 moves from the open position to the closed position. As shown in FIG. 2, a second portion 82 of the camming surface 58 extends parallel to the direction indicated by the letter B in which the door slides when moving from the closed position to the open position so the repository 32 stays in the dumping position until the door 60 nears a fully open position. As will be apparent to those skilled in the art, this configuration reduces the opportunity for a user to access the interior 14 of the receptacle 12 as the door 60 moves from the closed position to the open position. The first and second portions 80, 82 respectively of the camming surface 58 are joined by a smooth transitional portion 84 of the camming surface so the hopper smoothly moves between the holding position and the dumping position.

A slot 90 is provided in the chute 28 for receiving a hooked tongue 92 extending from the leading edge of the door 60. After the tongue 92 is fully engaged with the slot 90, the door 60 cannot be reopened. When the waste receptacle 32 is at capacity, the tongue 92 is inserted in the slot 90 to lock the door 60 in the closed position for disposal.

Although components of the present invention may be made of other materials without departing from the scope of the present invention, in one embodiment are formed from suitable plastics, such as polypropylene, polyethylene, and combinations thereof. The components may be colored in conformance with industry standards. The base and lid may be formed from any material having suitable leak and puncture resistance and may be partially or completely transparent or translucent to monitor the level of medical waste in the base.

To use the waste receptacle 10 of the present invention, a user drops medical waste W through the opening 26 in the cover 32. The medical waste W slides down the chute 28 under the force of gravity and into the intermediate waste receptacle 32 as shown in FIG. 1. The user then grasps the knob 62 and slides the door 60 from the open position to the closed position. As the door 60 closes, the intermediate waste receptacle 32 pivots downward into the interior 14 of the base 12 so the medical waste W slides down the lower wall 52 of the hopper into the interior of the base. Then the user, grasping the knob 62, slides the door 60 from the closed position to the open position so the receptacle 32 rotates back to the holding position in which it is ready for additional waste. Once the base 12 is deemed at capacity, the user grasps the knob 62 and moves the door 60 until the hooked tongue 92 is fully engaged in the slot 90 to lock the door 60 in the closed position for disposing the receptacle 10.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A lid for covering an interior of a medical waste receptacle base, said lid comprising:
a cover sized and shaped for covering the interior of the medical waste receptacle base, the cover having an opening sized for passing medical waste therethrough;
an intermediate waste repository connected to the cover, said repository being moveable between a holding position adapted for holding waste segregated from the receptacle base interior, and a dumping position adapted for biasing waste by gravity into the receptacle base interior;
a closure sized for blocking the opening operatively connected to the cover for movement between an open position, in which the closure is at least partially out of alignment with the opening to allow medical waste to pass through the opening toward the intermediate waste repository, and a closed position, in which the closure is aligned with the opening to block the opening to prevent medical waste from passing through the opening, the closure comprising a door slidably attached to the cover for movement between the open position and the closed position; and
a link operatively connecting the closure and the intermediate waste repository so the intermediate waste repository moves to the dumping position as the closure moves to the closed position and so the intermediate waste repository moves to the holding position as the closure moves to the open position.

2. A lid as set forth in claim 1 wherein the intermediate waste repository comprises a hopper pivotally mounted on the cover.

3. A lid as set forth in claim 2 wherein the cover includes a chute positioned for directing medical waste from the opening to the hopper when the waste repository is in the holding position.

4. A lid as set forth in claim 2 wherein the hopper comprises opposing walls at least in part defining a volume sized and shaped for receiving medical waste.

5. A lid as set forth in claim 4 wherein the cover includes a chute positioned for directing medical waste from the opening to the hopper when the waste repository is in the holding position.

6. A lid as set forth in claim 5 wherein the walls of the hopper include an upper wall, which engages a lower end of the chute when the repository is in the dumping position, and a lower wall, which engages the lower end of the chute when the repository is in the holding position.

7. A lid as set forth in claim 6 wherein the hopper is V-shaped.

8. A lid as set forth in claim 6 wherein the link comprises a cam connected to one of the closure and the intermediate waste repository and a follower operatively engaging the cam extending from another of the closure and the intermediate waste repository.

9. A lid as set forth in claim 8 wherein:
the cam is connected to the intermediate waste repository; and
the follower extends from the closure.

10. A lid as set forth in claim 9 wherein the cam extends downward from a lower surface of the upper wall.

11. A lid as set forth in claim 1 wherein:
the closure comprises an arm extending downward from the door and beside the upper wall of the hopper; and
the follower extends between the upper and lower walls of the hopper to engage the cam.

12. A lid as set forth in claim 11 wherein:
the cam includes a camming surface that the follower engages; and
a first portion of the camming surface extends parallel to a direction in which the door slides when moving from the open position to the closed position so the repository stays in the holding position until the door is between the open position and the closed position.

13. A lid as set forth in claim 12 wherein a second portion of the camming surface extends parallel to a direction in which the door slides when moving from the closed position to the open position so the repository stays in the dumping position until the door is between the closed position and the open position.

14. A lid as set forth in claim 13 wherein said first and second portions of the camming surface are joined by a smooth transitional portion of the camming surface.

15. A medical waste receptacle comprising:
a base having an interior sized and shaped for receiving medical waste;

a cover sized and shaped for covering the interior of the base, the cover having an opening sized for passing medical waste therethrough;

an intermediate waste repository connected to the cover, said repository being moveable between a holding position adapted for holding waste segregated from the receptacle base interior, and a dumping position adapted for biasing waste by gravity into the receptacle base interior;

a closure formed separately from the intermediate waste repository and sized for blocking the opening operatively connected to the cover for movement between an open position, in which the closure is at least partially out of alignment with the opening to allow medical waste to pass through the opening toward the intermediate waste repository, and a closed position, in which the closure is aligned with the opening to block the opening to prevent medical waste from passing through the opening; and a link operatively connecting the closure and the intermediate waste repository, said link moving the intermediate waste repository to the dumping position as the closure moves to the closed position and moving the intermediate waste repository to the holding position as the closure moves to the open position.

16. A lid for covering an interior of a medical waste receptacle base, said lid comprising:

a cover sized and shaped for covering the interior of the medical waste receptacle base, the cover having an opening sized for passing medical waste therethrough;

a closure sized for blocking the opening operatively connected to the cover for movement between an open position, in which the closure is at least partially out of alignment with the opening to allow medical waste to pass through the opening, and a closed position, in which the closure is aligned with the opening to block the opening to prevent medical waste from passing through the opening; and an intermediate waste repository operatively connected to the closure so the repository moves from a holding position adapted for holding waste segregated from the receptacle base interior to a dumping position adapted for biasing waste by gravity into the receptacle base interior as the closure moves to the open position and so the repository moves from the dumping position to the holding position as the closure moves to the closed position; and wherein the closure moves at least partway from the open position to the closed position before the repository moves from the holding position toward the dumping position.

17. A lid as set forth in claim 16 wherein the closure moves at least partway from the closed position to the open position before the repository moves from the dumping position toward the holding position.

18. A medical waste receptacle comprising:

a base having an interior sized and shaped for receiving medical waste;

a cover sized and shaped for covering the interior of the base, the cover having an opening sized for passing medical waste therethrough;

a closure sized for blocking the opening operatively connected to the cover for movement between an open position, in which the closure is at least partially out of alignment with the opening to allow medical waste to pass through the opening, and a closed position, in which the closure is aligned with the opening to block the opening to prevent medical waste from passing through the opening; and an intermediate waste repository operatively connected to the closure so the repository moves from a holding position adapted for holding waste segregated from the interior to a dumping position adapted for biasing waste by gravity into the interior as the closure moves to the open position and so the repository moves from the dumping position to the holding position as the closure moves to the closed position; and wherein the closure moves at least partway from the open position to the closed position before the repository moves from the holding position toward the dumping position.

19. A waste receptacle as set forth in claim 18 wherein the closure moves at least partway from the closed position to the open position before the repository moves from the dumping position toward the holding position.

* * * * *